United States Patent
Yao et al.

(10) Patent No.: US 11,974,809 B2
(45) Date of Patent: May 7, 2024

(54) NON-MYDRIATIC, NON-CONTACT SYSTEM AND METHOD FOR PERFORMING WIDEFIELD FUNDUS PHOTOGRAPHIC IMAGING OF THE EYE

(71) Applicant: THE BOARD OF TRUSTEES OF THE UNIVERSITY OF ILLINOIS, Urbana, IL (US)

(72) Inventors: Xincheng Yao, Hinsdale, IL (US); Devrim Toslak, Konyaalti/Antalya (TR)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 680 days.

(21) Appl. No.: 16/622,807

(22) PCT Filed: Jun. 13, 2018

(86) PCT No.: PCT/US2018/037281
§ 371 (c)(1),
(2) Date: Dec. 13, 2019

(87) PCT Pub. No.: WO2018/231947
PCT Pub. Date: Dec. 20, 2018

(65) Prior Publication Data
US 2021/0145276 A1 May 20, 2021

Related U.S. Application Data

(60) Provisional application No. 62/518,801, filed on Jun. 13, 2017.

(51) Int. Cl.
| A61B 3/12 | (2006.01) |
| A61B 3/00 | (2006.01) |
| A61B 3/14 | (2006.01) |
| A61B 3/15 | (2006.01) |
| G02B 13/14 | (2006.01) |
| G03B 30/00 | (2021.01) |

(52) U.S. Cl.
CPC ............. *A61B 3/12* (2013.01); *A61B 3/0008* (2013.01); *A61B 3/14* (2013.01); *A61B 3/152* (2013.01); *G02B 13/14* (2013.01); *G03B 30/00* (2021.01)

(58) Field of Classification Search
CPC .......... A61B 3/12; A61B 3/0008; A61B 3/14; A61B 3/152; G02B 13/14; G03B 30/00
See application file for complete search history.

(56) References Cited

U.S. PATENT DOCUMENTS

| 2006/0268231 A1 | 11/2006 | Gil et al. | |
| 2007/0159600 A1* | 7/2007 | Gil ....................... | A61B 3/0008 351/221 |

(Continued)

FOREIGN PATENT DOCUMENTS

| CN | 101569545 A | 11/2009 |
| CN | 103446676 A | 12/2013 |

(Continued)

OTHER PUBLICATIONS

Machine translation of KR 101855009 B1 (Year: 2018).*

(Continued)

*Primary Examiner* — Darryl J Collins
*Assistant Examiner* — Matthew Y Lee
(74) *Attorney, Agent, or Firm* — Thomas | Horstemeyer, LLP

(57) ABSTRACT

A non-mydriatic, non-contact ultra-widefield fundus (u-WF) photographic imaging system and method are provided for performing u-WF photographic imaging of the eye. The non-mydriatic, non-contact u-WF photographic imaging system includes an illumination system that delivers trans-pars-planar illumination to the eyeball. This frees the entire pupil to be used for imaging. Freeing the entire pupil to be used for imaging allows a u-WFC of the non-mydriatic, (Continued)

non-contact u-WF photographic imaging system to use a relatively simple optics system to capture an ultra-wide FOV. Eliminating the need to dilate the pupil and the need to make contact with the eye while performing imaging eliminates the many problems associated with mydriatic, contact-mode fundus imaging systems and methods. In addition, the system can be implemented in a way that makes it highly suitable for telemedicine applications in underserved areas where clinics and trained healthcare providers may not be available.

17 Claims, 12 Drawing Sheets

(56) References Cited

U.S. PATENT DOCUMENTS

| 2012/0050676 | A1* | 3/2012 | Saito | A61B 3/0008 |
| | | | | 351/246 |
| 2013/0128223 | A1* | 5/2013 | Wood | A61B 1/0684 |
| | | | | 351/246 |
| 2015/0342495 | A1* | 12/2015 | Davis | A61B 3/12 |
| | | | | 351/221 |
| 2016/0228001 | A1* | 8/2016 | Choate | A61B 3/0025 |
| 2019/0246986 | A1* | 8/2019 | Rodger | A61B 3/117 |
| 2019/0290124 | A1* | 9/2019 | Laforest | A61B 3/12 |

FOREIGN PATENT DOCUMENTS

| DE | 10349091 A1 | 5/2005 | |
| KR | 101855009 B1 * | 5/2018 | A61B 3/12 |
| WO | 2017151921 A1 | 9/2017 | |

OTHER PUBLICATIONS

International Search Report for PCT/US2018/037281, dated Oct. 19, 2018.

First Office Action issued by the Chinese Patent Office for application 2018800483855, dated Sep. 2, 2021.

* cited by examiner

NON-MYDRIATIC, NON-CONTACT SYSTEM AND METHOD FOR PERFORMING WIDEFIELD FUNDUS PHOTOGRAPHIC IMAGING OF THE EYE

CROSS-REFERENCE TO RELATED APPLICATIONS

This application is the 35 U.S.C. § 371 national stage application of Patent Cooperation Treaty (PCT) international application No. PCT/US/2018037281, filed Jun. 13, 2018, which claims priority to, and the benefit of the filing date of, a U.S. provisional application having U.S. provisional application Ser. No. 62/518,801, entitled "Nonmydriatic Single-Shot Widefield Fundus Camera with Trans-Pars Planar Illumination," which was filed on Jun. 13, 2017, both of which are hereby incorporated by reference herein in their entireties.

STATEMENT OF GOVERNMENT INTEREST

This invention was made with government support under Grant Nos. P30 EY001792, R01 EY023522, and R01 EY024628, awarded by the National Institutes of Health, and CBET-1055889 awarded by the National Science Foundation. The government has certain rights in this invention.

TECHNICAL FIELD OF THE INVENTION

The invention relates to an ultra-widefield fundus photography. More particularly, the invention relates to a non-mydriatic, non-contact system and method for performing ultra-widefield fundus photographic imaging of the eye.

BACKGROUND OF THE INVENTION

Widefield fundus photography is essential for screening diabetic retinopathy (DR), retinopathy of prematurity (ROP), choroidal masses and choroidal metastases, choroidal dystrophies, and other eye diseases that can produce morphological abnormalities at both central and peripheral areas of the retina. Conventional fundus cameras deliver illumination through the peripheral area of the pupil. These fundus cameras illuminate the interior of the eye by delivering light into the eyeball through the pupil. Furthermore, traditional fundus cameras utilize trans-pupillary illumination, i.e., a ring illumination pattern is projected onto the pupil plane. The trans-pupillary illumination makes the optical design very complex, and pupil dilation is typically required, i.e., the conventional fundus imaging systems and methods are mydriatic in nature.

After passing through the pupil, the light diverges and illuminates the posterior of the eye. To make the illumination on the retina homogenous, the diameter and divergence of the ring pattern on the pupil plane have to be carefully adjusted. This requires careful design and sophisticated construction of the optical imaging system. Because the pupil is shared by the illumination and image paths, the available field of view for fundus photography is limited. Additional challenges with trans-pupillary illumination include glare caused by reflection from the cornea and crystalline lens. In addition, dilation of the pupil may produce multiple symptoms, including, for example, difficulty focusing and glare for hours or even longer.

An illumination method known as trans-scleral illumination has been proposed as one alternative illumination method to achieve ultra-widefield fundus examination. Trans-scleral illumination delivers the illumination light to the region outside of the pupil, and thus can increase the available field of view (FOV) for fundus photography. An ultra-widefield fundus camera (u-WFC) is one that achieves an FOV that is equal to or greater than 90°. Trans-scleral illumination was firstly introduced by Oleg Pomerantzeff, M.D., in 1975, in a system that placed optical fibers in contact with the sclera at the pars plana area to deliver diffused homogenous illumination to the eyeball. More recently, a u-WFC known as the Panoret-1000™ fundus camera was used to perform trans-scleral illumination and was capable of capturing single-shot, ultra-widefield digital fundus images. Its image quality was competitive to that of trans-pupillary illumination fundus cameras and outperformed them in imaging patients with certain conditions, but failed to achieve wide acceptance due to complications associated with of contact-mode imaging (e.g., scratch damage to the cornea and sclera, contamination, inflammation) and difficulty in clinical operation.

It is technically difficult to construct ultra-widefield fundus imagers due in large part to the technical complications of the illumination and imaging mechanisms. The high cost of fundus instruments and clinical complication of pupil dilation limit the access to routine examination, particularly for rural and underserved areas, where both skilled ophthalmologists and expensive instruments are typically unavailable.

DETAILED DESCRIPTION

Figure 1:
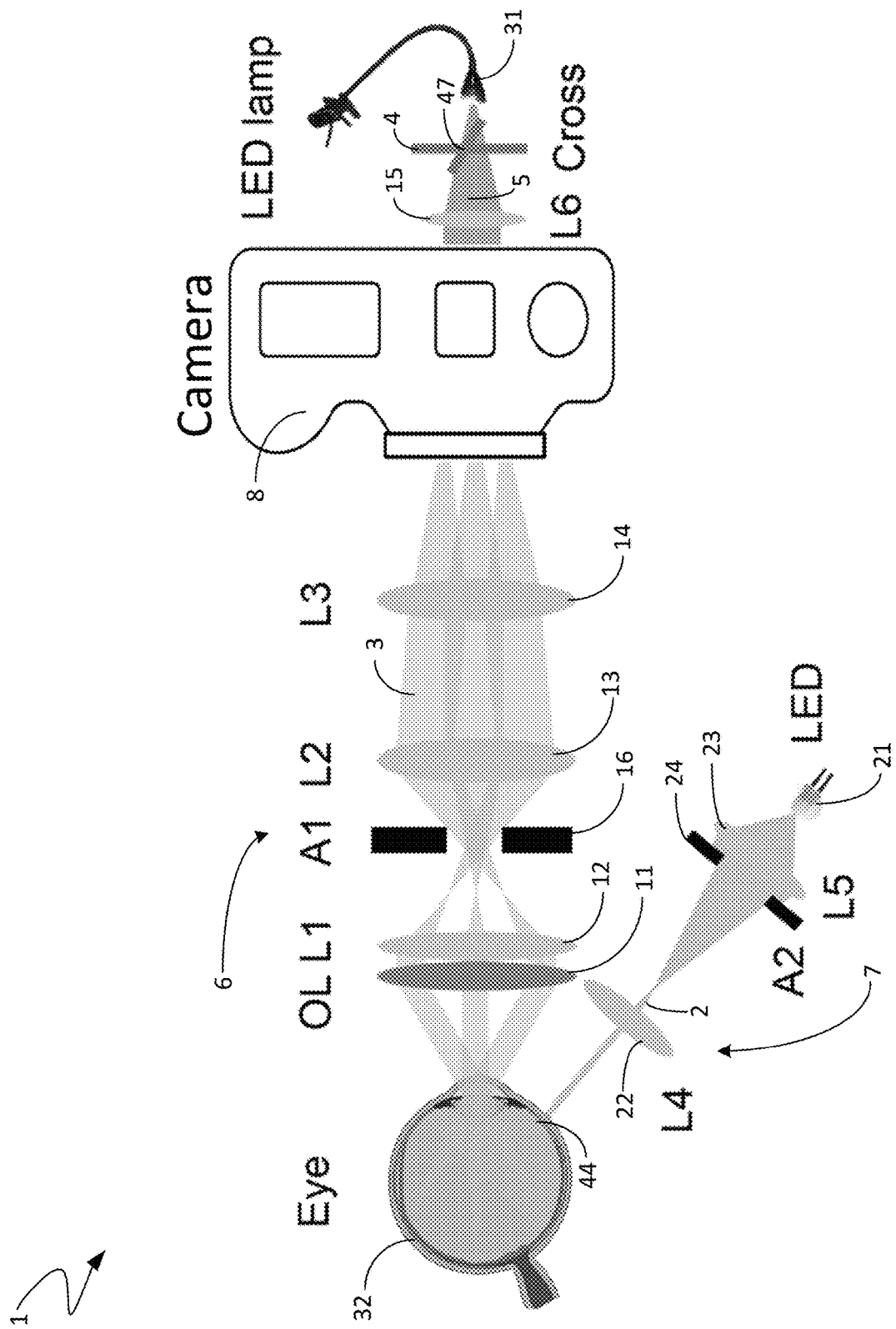
FIG. 1 illustrates a schematic diagram of the non-mydriatic, non-contact ultra-widefield photographic imaging system in accordance with a representative embodiment.

In accordance with representative embodiments, a non-mydriatic, non-contact ultra-widefield fundus (u-WF) photographic imaging system and method are provided for performing u-WF photographic imaging of the eye. The non-mydriatic, non-contact u-WF photographic imaging system includes an illumination system that delivers trans-pars-plana illumination to the eyeball, thereby freeing the entire pupil to be used for imaging. Freeing the entire pupil to be used for imaging allows a u-WFC of the non-mydriatic, non-contact u-WF photographic imaging system to use a relatively simple optics system to achieve an ultra-wide FOV for imaging. Eliminating the need to dilate the pupil and the need to make contact with the eye eliminates the aforementioned problems associated with mydriatic, contact-mode fundus imaging systems and methods.

In addition, the system can be implemented in a way that makes it highly suitable for telemedicine applications in underserved areas where clinics and trained healthcare providers may not be available. In particular, the non-mydriatic, non-contact u-WF photographic imaging system can be made relatively easy to use, portable, and relatively inexpensive, which make the system highly suitable for telemedicine applications in underserved areas.

In the following detailed description, for purposes of explanation and not limitation, example embodiments disclosing specific details are set forth in order to provide a thorough understanding of an embodiment according to the present teachings. However, it will be apparent to one having ordinary skill in the art having the benefit of the present disclosure that other embodiments according to the present teachings that depart from the specific details disclosed herein remain within the scope of the appended claims. Moreover, descriptions of well-known apparatuses and methods may be omitted so as to not obscure the description of the example embodiments. Such methods and apparatuses are clearly within the scope of the present teachings.

The terminology used herein is for purposes of describing particular embodiments only, and is not intended to be limiting. The defined terms are in addition to the technical and scientific meanings of the defined terms as commonly understood and accepted in the technical field of the present teachings.

As used in the specification and appended claims, the terms "a," "an," and "the" include both singular and plural referents, unless the context clearly dictates otherwise. Thus, for example, "a device" includes one device and plural devices.

Relative terms may be used to describe the various elements' relationships to one another, as illustrated in the accompanying drawings. These relative terms are intended to encompass different orientations of the device and/or elements in addition to the orientation depicted in the drawings.

It will be understood that when an element is referred to as being "connected to" or "coupled to" or "electrically coupled to" another element, it can be directly connected or coupled, or intervening elements may be present.

The term "memory" or "memory device", as those terms are used herein, are intended to denote a computer-readable storage medium that is capable of storing computer instructions, or computer code, for execution by one or more processors. References herein to "memory" or "memory device" should be interpreted as one or more memories or memory devices. The memory may, for example, be multiple memories within the same computer system. The memory may also be multiple memories distributed amongst multiple computer systems or computing devices.

A "processor", as that term is used herein encompasses an electronic component that is able to execute a computer program or executable computer instructions. References herein to a computer comprising "a processor" should be interpreted as a computer having one or more processors or processing cores. The processor may for instance be a multi-core processor. A processor may also refer to a collection of processors within a single computer system or distributed amongst multiple computer systems. The term "computer" should also be interpreted as possibly referring to a collection or network of computers or computing devices, each comprising a processor or processors. Instructions of a computer program can be performed by multiple processors that may be within the same computer or that may be distributed across multiple computers.

Exemplary, or representative, embodiments will now be described with reference to the figures, in which like reference numerals represent like components, elements or features. It should be noted that features, elements or components in the figures are not intended to be drawn to scale, emphasis being placed instead on demonstrating inventive principles and concepts.

Experimental Setup

Figure 2:
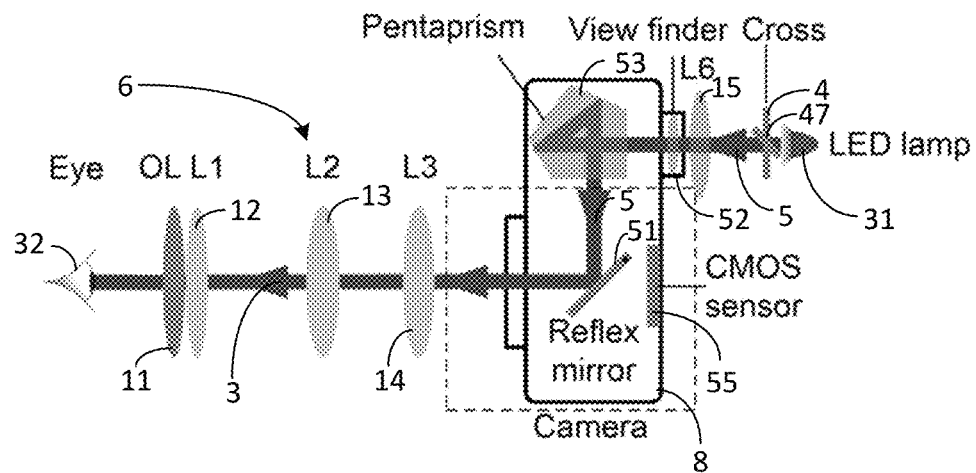
FIG. 2 is a schematic diagram showing the imaging light path and the light path for the fixation target for the system shown in FIG. 1.
Figure 3:
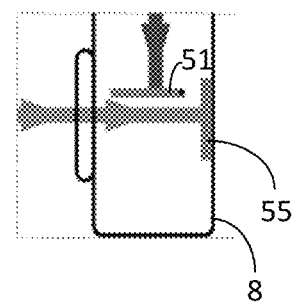
FIG. 3 shows a portion of the schematic diagram shown in FIG. 2 with a reflex mirror moved out of the imaging light path.

FIG. 1 illustrates a schematic diagram of the non-mydriatic, non-contact u-WF photographic imaging system 1 in accordance with a representative embodiment showing the illumination light path 2, the imaging light path 3, and a fixation target 4. FIG. 2 is a schematic diagram showing the imaging light path 3 and the light path 5 for the fixation target 4 for the system 1 shown in FIG. 1. FIG. 3 shows a portion of the schematic diagram shown in FIG. 2 with a reflex mirror moved out of the imaging light path 3.

The system 1 includes an imaging system 6 and an illumination system 7. The imaging system 6 includes a camera 8 and an optics system that includes at least one optical element. In accordance with this embodiment, the optics system of the imaging system 6 includes multiple optical elements, including an ophthalmic lens (OL) 11, refractive lenses L1 12, L2 13, L3 14 and L6 15, and a circle aperture A1 16. The illumination system 7 includes a light source 21 and an optics system that includes at least one optical element. In accordance with this embodiment, the optics system of the illumination system 7 includes multiple optical elements, including refractive lenses L4 22 and L5 23 and an annular aperture A2 24.

In accordance with this embodiment, the light source 21 is at least one light emitting diode (LED) that produces white light. In accordance with this representative embodiment, the fixation target 4 is backlit with a light source 31, which is typically an LED. The backlit fixation target 4 is used to cause the subject, which in this case is a human being, to bring his or her eye 32 to focus at a location that will produce the best imaging results.

For the experimental setup depicted in FIGS. 1-3, a 565 nanometer (nm) LED was chosen as the light source 21 for color fundus imaging. This particular LED displays green and red colors, depending on the amount of electrical current that is delivered to the LED. Thus, in the experimental setup, the LED that was used emitted green light or red light based on the current delivered to the LED via a green channel and a red channel, respectively.

Light from the LED 21 was collimated by L5 23 and passed through the arc-shaped aperture A2 24. The lens L4 22 was used to image the aperture onto the sclera to form an arc-shaped illumination pattern. The arc-shaped aperture A2 24 was carefully designed to closely match the shape of the pars plana 44. In the experimental setup, the end of an illuminating arm that was close to the eye 32 and that was used to hold the illumination system 7 could be manually moved in a horizontal direction to precisely deliver illumination light to the pars plana 44. It should be noted that the optical element that is closest to the eye that couples the light onto the pars plana 44, which is the lens L4 22 in the experimental setup, is spaced a predetermined distance from the eye 32 to avoid physical contact with the eyeball and with the eyelid (not shown) of the eye 32.

Light passing through the pars plana 44 was diffused and illuminated the intraocular area homogenously. The OL 11, which was a 22D ophthalmic lens made by Volk Optical, Inc. in the experimental setup, was used to collect light coming out of the pupil. Three off-the-shelf lenses L1 12, L2 13 and L3 14 were placed after the OL 11 to relay the fundus image onto an optical sensor array of the camera 8. In the experimental setup, the optical sensor array of the camera 8 was a Complementary Metal Oxide Semiconductor (CMOS) array of sensors and the camera 8 was a digital single-lens reflex camera having model number EOS Rebel T6i, manufactured by Canon Inc.

The aperture A1 16 was placed at the pupil conjugate plane to restrict the effective imaging pupil size. In the experimental setup, the aperture A1 16 was configured to restrict the effective imaging pupil size to 2.5 mm for best imaging resolution, as well as to reject scattering light from the sclera. The lens L6 15 was positioned behind the camera viewfinder and a cross 46 was illuminated by the light source 31 placed in front of the lens L6 15 to serve as a fixation target so that the testing subjects could fix their eyes by looking into the camera 8 through the lenses. A single-shot fundus image was easily acquired by pressing the shutter button of the camera 8.

In conventional fundus cameras, a beam splitter can be used to split the imaging and fixation light paths so that a fixation target can be employed. However, a beam splitter wastes a fraction of the light from the retina. In the experimental setup, no beam splitter was required due to the single reflex feature of the camera 8.

Instead, as shown in FIGS. 2 and 3, a reflex mirror 51 was used in the experimental setup to divert the light from the imaging light path 3 to the fixation target light path 5. During target fixation, the reflex mirror 51 is in the position shown in FIG. 2 so that the eye 32 can focus on the cross 47 of the fixation target 4. In accordance with this embodiment, the camera 8 included a view finder 52 and a pentaprism 53 positioned along the fixation light path 5. When shutter button of the camera is pressed, the reflex mirror 51 temporarily flips up as shown in FIG. 3 and light coming out from the eye 32 reaches the optical sensor array 55 of the camera 8, which produces a fundus image.

Figure 4:
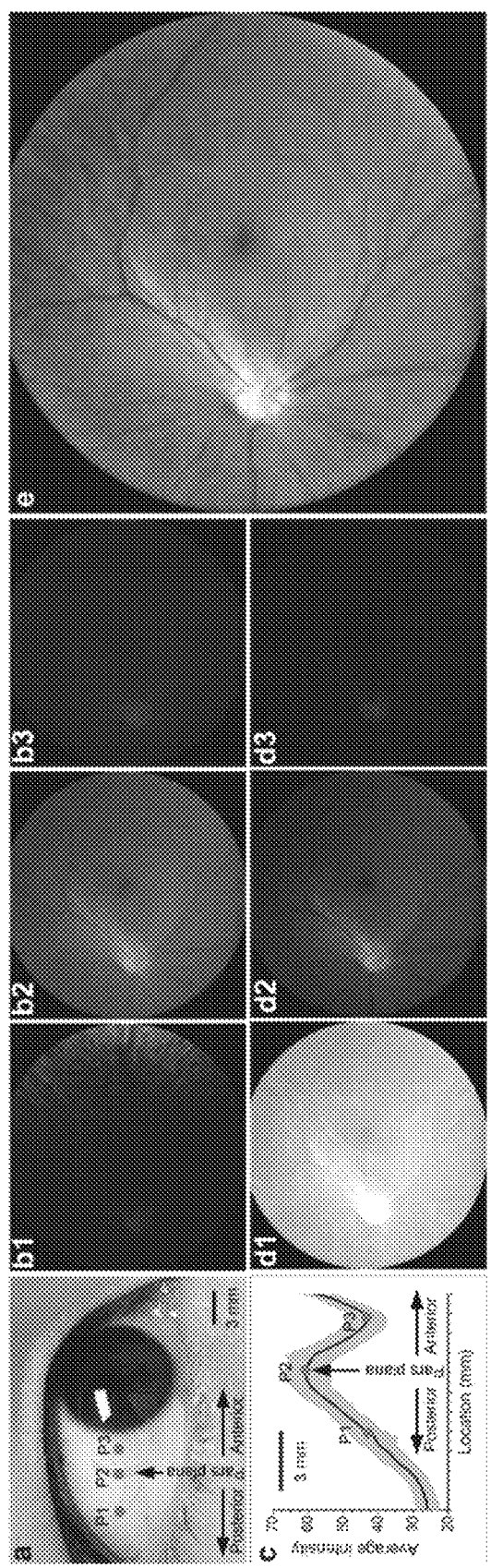
FIG. 4 shows various fundus images captured by the camera 8 of the system 1 shown in FIGS. 1-3 for different illumination locations and demonstrates the importance of properly illuminating the pars plana.

FIG. 4 shows various fundus images captured by the camera 8 of the system 1 shown in FIGS. 1-3 for different illumination locations and demonstrates the importance of properly illuminating the pars plana. Photo "a" in FIG. 4 three different illumination locations on the eye labeled "P1," "P2," and "P3." The images labeled "b1"-"b3" were acquired by the camera 8 at locations "P1"-"P3," respectively. The chart labeled "c" in FIG. 4 shows the average intensity of fundus images collected with constant power illumination delivered through different locations. The curve in chart "c" represents an average of five trials from one subject. The gray shadow in chart "c" represents the standard deviation. The images labeled "d1," "d2," and "d3" were captured using red light, green light and blue light, respectively. The image labeled "e" corresponds to normalized fundus image "b2," with digital compensation of red and green channel intensities. Macula, optic disc, nerve fiber bundles and blood vessels could be clearly identified in image "e."

As shown in photo "a," one arc-shaped visible light pattern was used for trans-pars-plana illumination. Fundus images "b1," "b2," and "b3" collected with illumination delivered through areas posterior, center and anterior, respectively, to the pars plana area. For all of these three images, the camera 8 was set to an exposure time of 1 second (s), with ISO 3200 and white balance color temperature 3200 K. It was observed that the image quality was sensitive to illumination location. By pointing the illumination pattern to the posterior of pars plana, choroidal vasculatures were observed in the fundus image dominated by red color (image "b1"). By moving the illumination pattern to the center of the pars plana area (location "P2"), retinal vasculatures, the optic disc, and the macula were unambiguously observed (image "b2"). Localizing the illumination pattern to the anterior of the pars plana area (location "P3"), the image was too dim to reveal details of fundus structures (image "b3"). In order to quantify the location-dependent efficiency of light illumination, average pixel intensities of individual images, which were collected with illumination pattern scanned from the posterior sclera to the limbus at a step interval of ~0.4 mm, were illustrated in chart "c."

All images in FIG. 4 were red predominated because of the superior penetration capability of the long (e.g., red) wavelength light, compared to short (e.g., green and blue) wavelengths of light. For image "b2," the average intensity of the red channel was 4 and 16 times higher than that of the green and blue channels, respectively. In order to enhance the visualization of retinal structures, red and green channels were digitally balanced in image "e." Given the absence of blue light in the light source in the prototype instrument, the blue channel was ignored to reconstruct the enhanced image "e." In image "e," macula and optic disc were clearly observed, and individual blood vessels were unambiguously identified. Moreover, nerve fiber bundles could also be observed as stripped patterns coming from the optic disc.

Quantitative Analysis of Widefield Fundus Image

Quantitative analysis of fundus images is essential for objective and automated classification of eye diseases. In order to verify the potential feasibility of using the trans-pars-planar illumination based on the fundus camera for quantitative imaging, the inventors explored automated classification of arteries and veins, quantitative analysis of blood vessel diameter and tortuosity, and arteriolar-to-venular diameter ratio (AVR). It is known that retinopathy can affect arteries and veins differently. For example, some studies have shown that in ROP the increase in arterial tortuosity is more significant than that of veins, and in DR the diameter of arteries decrease and diameter of veins increase. Therefore, separate analysis of arteries and veins can provide improved sensitivity for quantitative fundus image analysis and classification.

Figure 5:
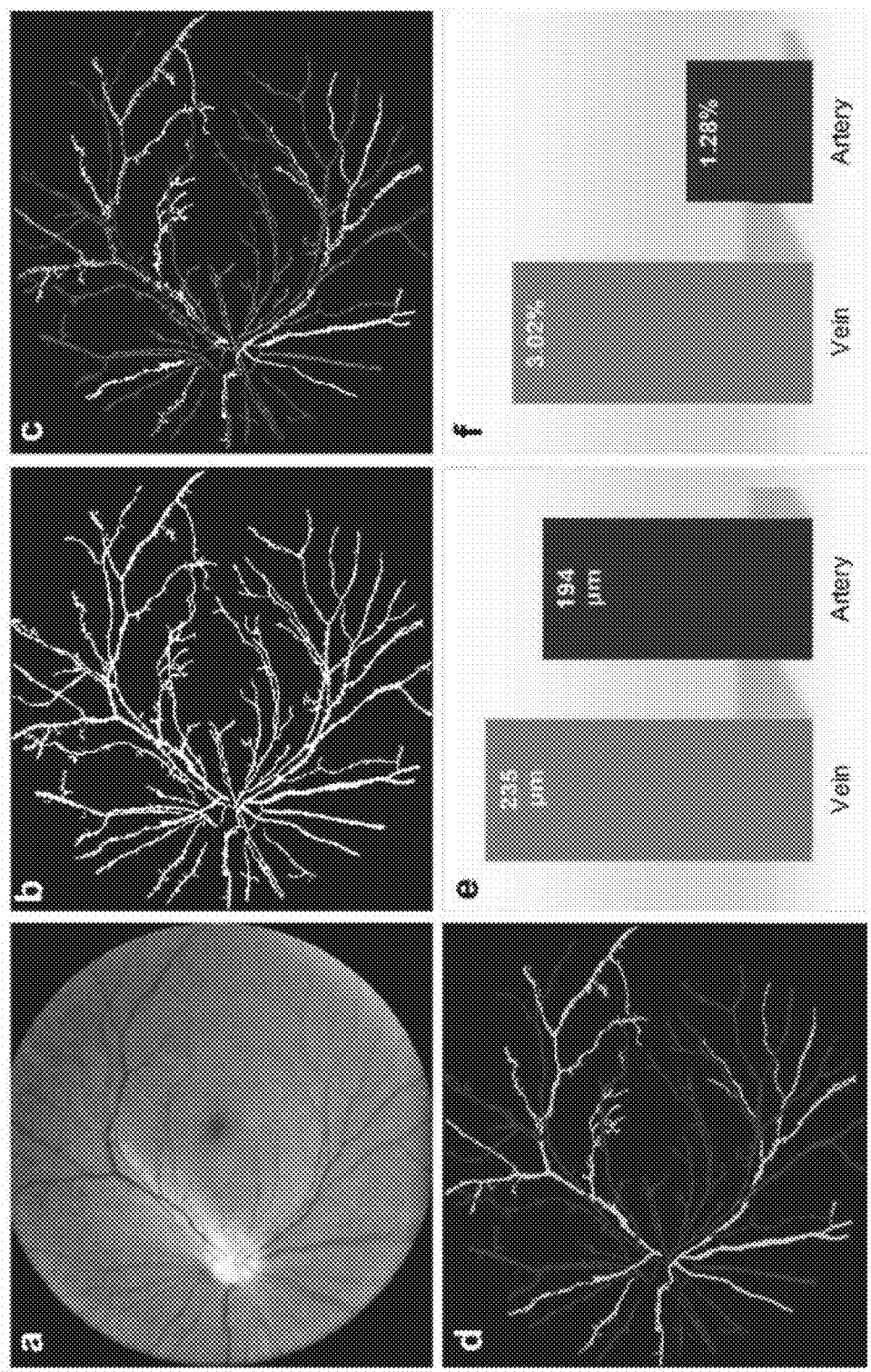
FIG. 5 depicts the manner in which an automated classification algorithm performed by a suitable processor classifies arteries and veins of the widefield fundus image "b2" shown in FIG. 4.

FIG. 5 depicts the manner in which an automated classification algorithm performed by a suitable processor classifies arteries and veins of the widefield fundus image "b2" shown in FIG. 4. Image "a" in FIG. 5 represents the green channel of the fundus image "b2" shown in FIG. 4, and is the same image as image "d2" in FIG. 4, but with brightness increased for better visualization. Image "b" in FIG. 5 is a segmented blood vessel map obtained using the green channel for image "a" of FIG. 5. Image "c" in FIG. 5 is an optical density ratio map of the red and green channels for the image "b" shown in FIG. 5. Image "d" in FIG. 5 shows arteries (red) and veins (cyan) classified by the automated classification algorithm. Chart "e" in FIG. 5 shows the average artery and vein diameters for the arteries and veins shown in image "d" of FIG. 5. Chart "f" in FIG. 5 shows the average artery and vein tortuosity for the arteries and veins shown in image "d" of FIG. 5.

The automated classification algorithm may be performed as follows. First, the red and green channels are separated from a color fundus image (image "b2" in FIG. 4). Second, the green channel is used to segment individual blood vessels for image "a" shown in FIG. 5 to reconstruct the blood vessel map shown in image "b" of FIG. 5. Third, the optical density ratio (ODR) between red and green channels was calculated. As shown in image "c" of FIG. 5, arteries showed a lower ODR value than veins. Fourth, a brightness threshold was applied to image "c" shown in FIG. 5 to separate arteries and veins, as depicted by image "d" shown in FIG. 5.

The automated classification algorithm reasonably matched manual classification processes of arteries and veins. The average diameters of arteries and veins is shown in chart "e" of FIG. 5. Thus, the AVR could be calculated as AVR=194 μm/235 μm=0.8, which is within the normal range (0.54-0.82) reported in previous publications.

Figure 6:
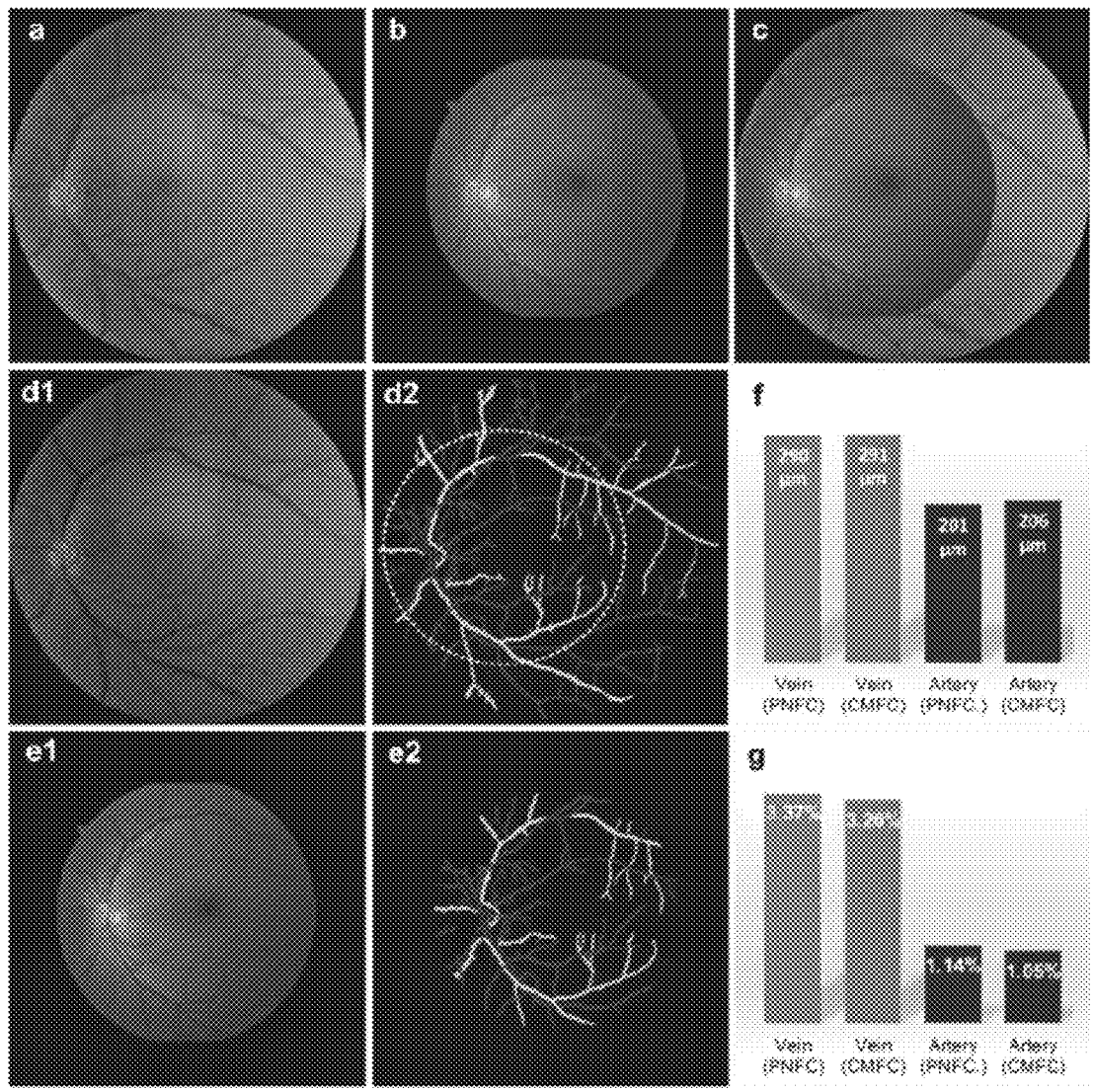
FIG. 6 depicts a comparative evaluation between the non-mydriatic, non-contact system 1 described above with reference to FIGS. 1-3 and a clinical mydriatic fundus camera.

FIG. 6 depicts a comparative evaluation between the non-mydriatic, non-contact system 1 described above with reference to FIGS. 1-3 and a clinical mydriatic fundus camera. Image "a" shown in FIG. 6 is a fundus image captured with the system 1 with 90° FOV (eye-angle, i.e., 60° external-angle). Image "b" shown in FIG. 6 is a fundus image captured from the same subject using a clinical mydriatic fundus camera, model number Cirrus Photo 800, manufactured by Zeiss, which has a FOV of 67.5° (eye-angle, i.e., 45° external-angle). Image "c" shown in FIG. 6 is an overlapping of images "a" and "b" of FIG. 6 for FOV comparison. Image "d1" shown in FIG. 6 corresponds to the green channel. Image "d2" shown in FIG. 5 shows classified arteries (red) and veins (cyan) of fundus image "a." Image "e1" shown in FIG. 6 corresponds to the green channel for image "b" shown in FIG. 6. Image "e2" shown in FIG. 6 shows classified arteries (red) and veins (cyan) for fundus image "b" shown in FIG. 6.

Chart "f" shown in FIG. 6 gives the average artery (red) and vein (cyan) diameters for the veins and arteries in image "d2" of FIG. 6 (dashed white circle area) and chart "g" shown in FIG. 6 shows the average artery (red) and vein (cyan) tortuosity for the veins and arteries shown in image "e2" of FIG. 6.

Comparative Evaluation Between the Lab Prototype Non-Mydriatic, Non-Contact Instrument and a Clinical Mydriatic Fundus Camera The expanded FOV (60° external-angle, i.e., 90° eye-angle) of the system 1 shown in FIGS. 1-3 was directly observed in the overlapped image "c" of FIG. 6. Fundus images captured with two systems revealed similar blood vessels, macula and optic disc. Particularly, the enhanced green channel (image "d1" compared to image "e1" in FIG. 6) and artery-vein classification (image "d2" compared to image "e2" in FIG. 6) show almost exactly the same retinal vasculatures in the overlapping area. Quantitative analysis of vessel diameter (chart "f" compared to chart "g" in FIG. 6) and tortuosity of the overlapping area further confirmed the great agreement between the non-mydriatic, non-contact system 1 and the clinical mydriatic fundus camera.

Figure 7:
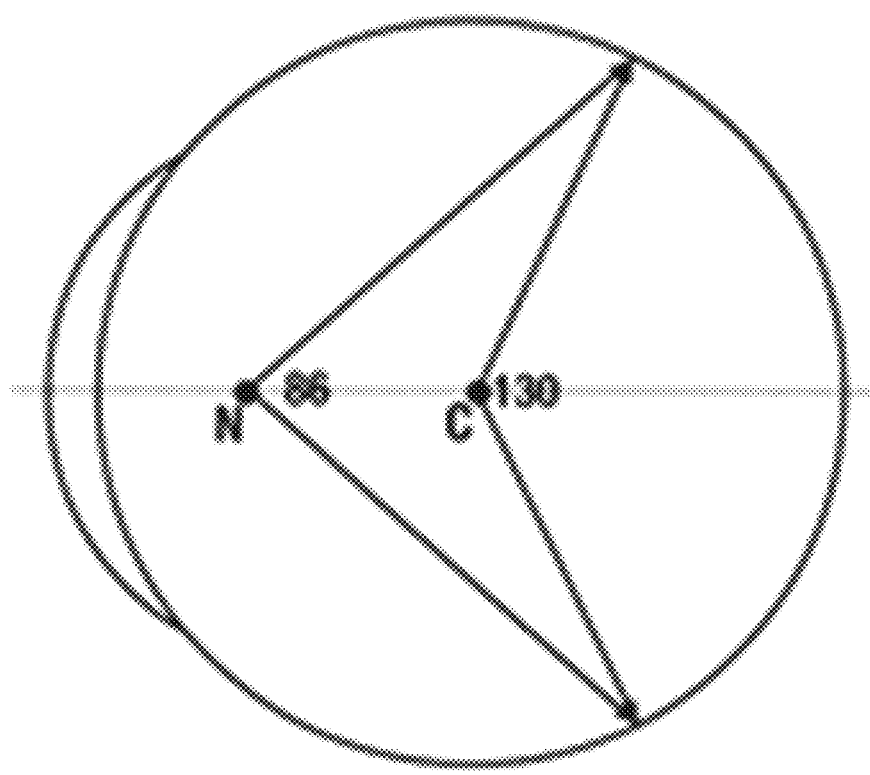
FIG. 7 is a schematic illustration of view fields in traditional fundus cameras defined relative to a nodal point, N, and for Retcam/Optos systems defined relative to the spherical center, C.

FIG. 7 is a schematic illustration of view fields in traditional fundus cameras defined relative to a nodal point, N, and for Retcam/Optos systems defined relative to the spherical center, C. A 130° view of Retcam/Optos systems is equivalent to 86° in traditional fundus cameras. As shown in FIG. 7, there are two methods to define fundus view. In traditional fundus cameras, the view angle based on the external angle is defined relative to the nodal point, N. However, for recent ultra-widefield instruments such as the Optos (Optos, Marlborough, MA) and Retcam (Clarity Medical Systems, Pleasanton, CA) systems, the spherical center, C, is used to define the view angle (i.e., internal angle). The relationship between the external and internal angles can be quantified as $\theta_{interior}=0.74\times 2\times\theta_{external}$. For example, the 130° view of single-shot Retcam image is equivalent to 86° view in traditional fundus photography. For easy comparison to the Optos and Retcam images, the FOV of the system 1 shown in FIGS. 1-3 is defined in terms of the internal angle standard to quantify fundus view field in following discussion.

Figure 8:
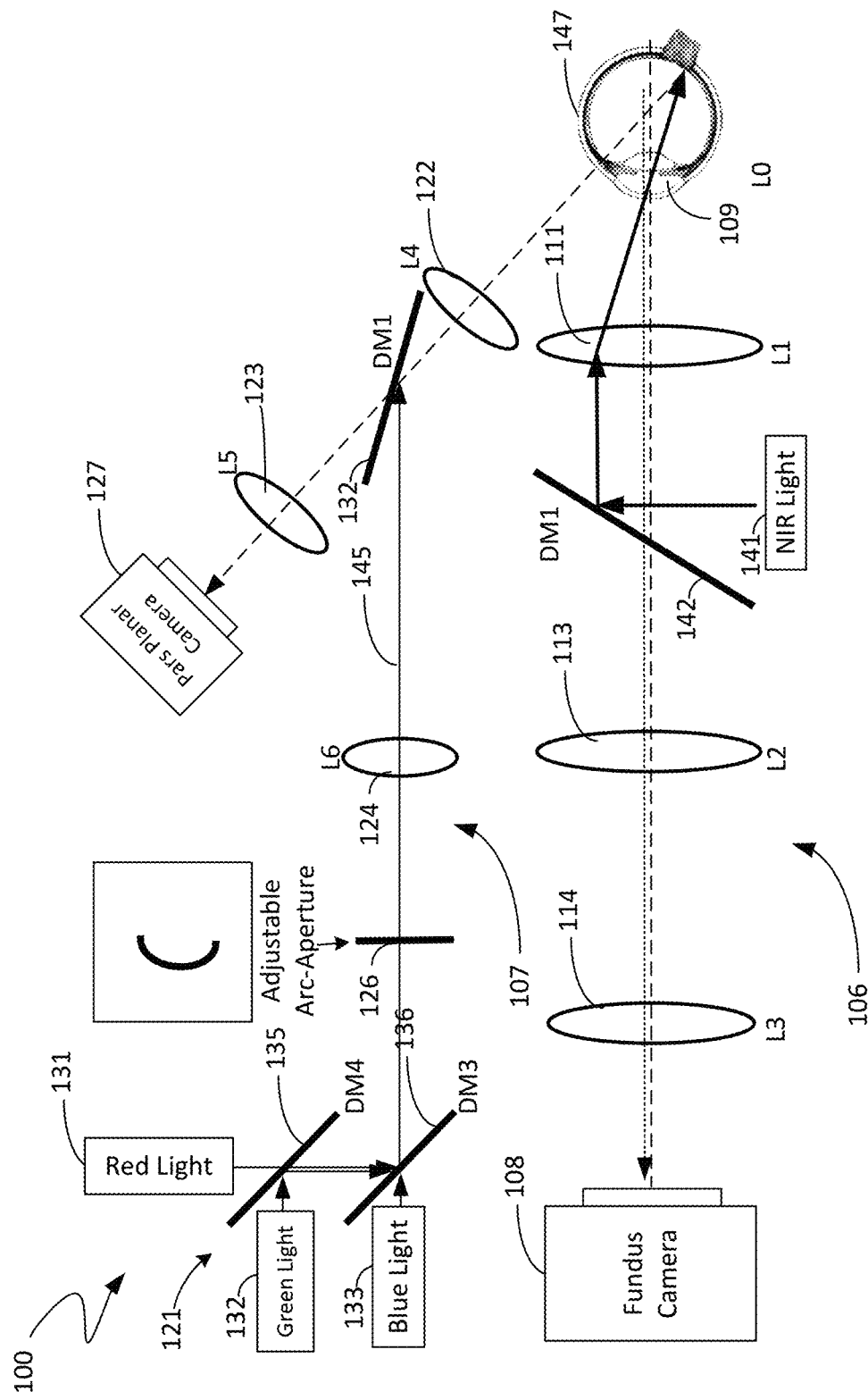
FIG. 8 illustrates a schematic diagram of the non-mydriatic, non-contact u-WF photographic imaging system 100 in accordance with another representative embodiment.

FIG. 8 illustrates a schematic diagram of the non-mydriatic, non-contact u-WF photographic imaging system 100 in accordance with another representative embodiment. In accordance with this embodiment, an illumination stage of the system 100 includes one or more optical elements and an additional optical sensor array for automatically locating the pars plana area of the eye to ensure that the light that is used to illuminate the eye for imaging is precisely directed onto the pars plana area.

The system 100 includes an imaging system 106 and an illumination system 107. The imaging system 106 includes a camera 108 and an optics system that includes at least one optical element. In accordance with this embodiment, the optics system of the imaging system 106 includes multiple optical elements, including lens L0 109, L1 111, L2 113, L3 114 and a beam splitter 116. The illumination system 107 includes a light source 121 and an optics system that includes at least one optical element. In accordance with this embodiment, the optics system of the illumination system 107 includes multiple optical elements, including lenses L4 122, L5 123, L6 124, an arc-shaped aperture 126, and an optical sensor array 127. In accordance with this embodiment, the light source 121 includes red, green and blue LEDs 131, 132 and 133, respectively, and first and second dichroic mirrors (DM) 135 and 136, respectively.

In accordance with a representative embodiment, the system 100 has an FOV of 150°, captures a single-shot fundus image, with a resolution of 20 pixels/degree (10 micrometers/pixel, corresponding to 20 micrometer system resolution), with a speed of 14 frames/second, and performs automatic identification of the pars plana.

In order to achieve the 150° FOV with 20 pixels/degree resolution, the optical sensor array of the camera 108 should have a frame resolution of at least 3000×3000 pixels. For the representative embodiment shown in FIG. 8, a model PL-D7715CU camera manufactured by PixeLINK of Ottawa, Canada was used. The model PL-D7715CU has a frame resolution at 4384×3288 pixels, with 1.4 μm×1.4 μm pixel size and a 14 fps frame rate.

The resolution of the system 100 is affected by both the digital camera (pixel resolution) and the optics system (diffraction limit). For a resolution of 20 pixels per degree, one external degree of visual angle is equal to 288 μm on the retina. As indicated above, the relationship between the external and interior angles can be quantified as $\theta_{interior}=0.74\times2\times\theta_{external}$. Therefore, the corresponding pixel resolution $R_p$ can be estimated as:

$$R_p = 288/(20\times0.74\times2) \approx 10 \text{ μm/pixel} \quad (1)$$

By considering the Nyquist law, the 10 μm/pixel corresponds to a 20 μm system resolution. In principle, the 20 μm system resolution should be also supported by the optics system. In other words, the diffraction limited resolution should be less than or equal to 20 μm to ensure that the 20 μm system resolution is obtained.

For estimating diffraction limited resolution, the effect of the pupil diameter, i.e., effective numeric aperture (NA) of ocular lens on optical resolution should be considered. In accordance with the representative embodiment shown in FIG. 8, a pupil diameter of $D_p=1.5$ mm was used. The optical power of entire eye is 60 diopters, which corresponds to an optical length $f_0 \approx 17$ mm. Therefore, optical resolution of the retinal image can be estimated as:

$$R_o = 1.22\lambda \cdot \frac{f_o}{D_p} \quad (2)$$

Substituting $D_p=1.5$ mm, $f_0=17$ mm, and $\lambda=550$ nm, diffraction limited optical resolution is theoretically estimated at $R \approx 8$ μm. However, it is known that optical aberrations of the eye can degrade practical resolution of the retinal imaging system. A conservative estimation of the system resolution is a 20 μm.

Figure 9:
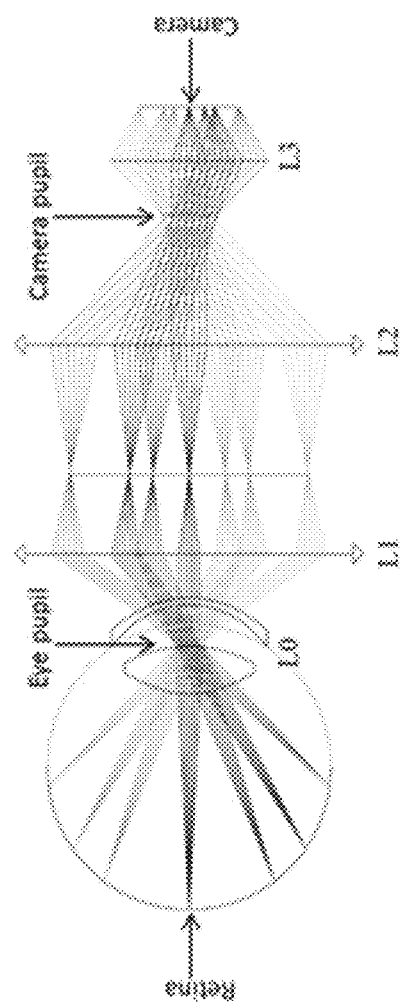
FIG. 9 is a schematic diagram of the optics system of the imaging system shown in FIG. 8.

FIG. 9 is a schematic diagram of the optics system of the imaging system 106 shown in FIG. 8. For a pixel size of the camera 108 of 1.4 μm, the pixel resolution is 10 μm. Therefore, optical magnification (from the retina to the camera 108) should be Mr=1.4/10=0.14. For this representative embodiment, the optical magnification of the optics can be quantified as:

$$Mr = \frac{f1 \cdot f3}{f0 \cdot f2} = 0.14 \quad (3)$$

where $f_0, f_1, f_2, f_3$ are focal lengths of the lenses L0 109, L1 111, L2 113, L3 114, respectively. For this example embodiment, it is assumed that $f_0=17$ mm; $f_1=12$ mm; $f_2=30$ mm, and thus $f_3=6$ mm.

With reference again to FIG. 8, the system 100 also includes a light source 141 and a DM 142. During fundus imaging, the red, green and blue light produced by the red, green and blue LEDs 131-133, respectively, is combined via optical effects performed by the DMs 135 and 136 to produce white light and directed along an illumination light path 145. The arc-shaped aperture 126 converts the light beam into an arc-shaped light beam to match the shape of the pars plana area of the eye 147. The combined optical effects of lens L6 124, DM 132 and lens L4 122 redirect the illumination light path toward the pars plana area and cause the size of the arc-shaped beam to match the size of the pars plana area. Thus, the arc-shaped light beam is made to match the size and shape of the pars plana area.

The illumination light passes through the pars plana area, is diffused, illuminates the intraocular area homogenously and is reflected through the pupil of the eye. Light reflected through the pupil is directed by the optics system 109, 111, 142, 113 and 114 of the imaging system 106 onto the optical sensor array of the fundus camera 108, which acquires the fundus image having the characteristics described above with reference to FIGS. 5 and 6.

Figure 10:
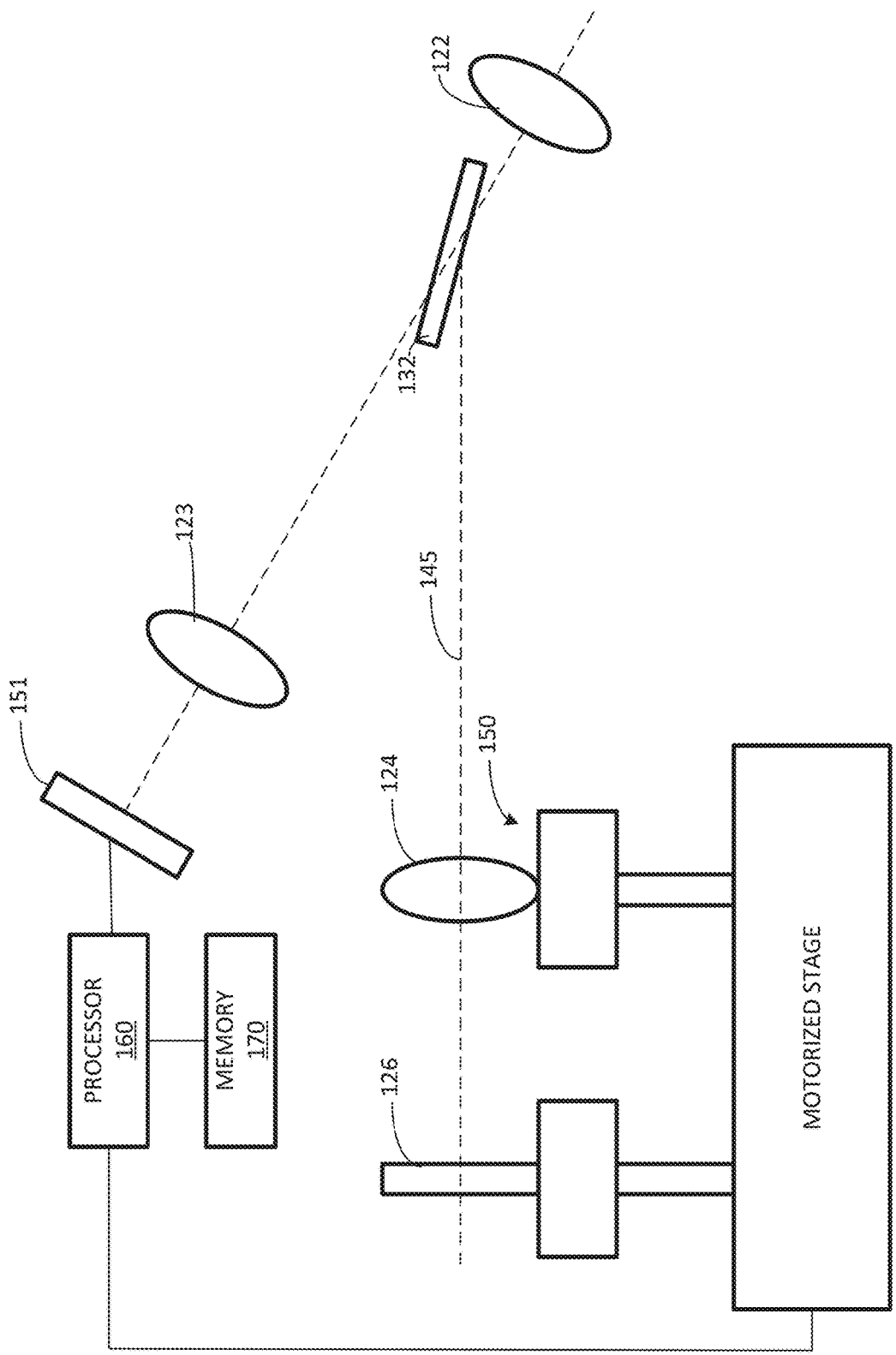
FIG. 10 illustrates a block diagram of the illumination system of the system 100 shown in FIG. 8 in accordance with a representative embodiment in which the system includes an motorized stage for adjusting the position of one or more optical elements based on a determination by a processor that the illumination light beam being directed onto the eye is not properly aligned with the pars plana area of the eye.

As indicated above, in accordance with an embodiment, the system 100 shown in FIG. 8 has the ability to automatically locate the pars plana area. FIG. 10 illustrates a block diagram of the illumination system 107 of the system 100 shown in FIG. 8 in accordance with a representative embodiment in which the system 100 includes an motorized stage 150 for adjusting the position of optical elements 124 and/or 125 based on a determination by a processor 160 of the system 100 that the illumination light beam being directed onto the eye 147 is not properly aligned with the pars plana area of the eye 147. The processor 160 can perform different algorithms to make this determination, a few examples of which are described below.

With reference to FIGS. 8 and 10, during an alignment process, the light source 141, which is typically a near infrared (NIR) light source (e.g., an NIR-emitting LED), emits an light beam that is directed by the DM 142 and lens L1 111 through the pupil. Light reflected from the intraocular region of the eye 147 passes out of an area of the eye 147 that includes the pars plana area. Optical effect of the lens 122, the DM 132 and the lens 123 cause the reflected light to be directed onto an optical sensor array 151 of the camera 127.

The processor 160 performs an algorithm that processes the image output from the optical sensor array 151 and determines whether the optical element 124 and/or the optical element 126 is properly aligned with the pars plana area. If not, the processor 160 causes the motorized stage 150 to adjust at least one of the X, Y and Z positions of the optical element 124 and/or the optical element 126 until proper alignment is achieved.

In addition, the arc-shaped aperture 126 may be adjustable to allow the width of the arc-shaped pattern formed by the arc-shaped aperture 126 to be adjusted by the processor 160 to match the size of the pars plana area As an alternative to the algorithm described above, the processor 160 may also be in communication with the fundus camera 108 to allow the processor 160 to adjust the X, Y and/or Z position of the optical element 124 and/or the optical element 126 based on fundus images acquired by the fundus camera 108. In accordance with this embodiment, retinal images captured by the fundus camera 108 continuously or at adjacent instants in time during the illumination scanning are processed by the processor 160. The light level within each retinal image is dependent on the illumination location. After collecting retinal images, overall image intensity can be readily computed by the processor 160 and the image with maximal light intensity can be determined, which corresponds to the location of pars plana. The processor 160 can then cause the motorized stage 150 to adjust the position of optical element 124 and/or of optical element 126 to the position that corresponds to the image with maximum light intensity.

Figure 11:
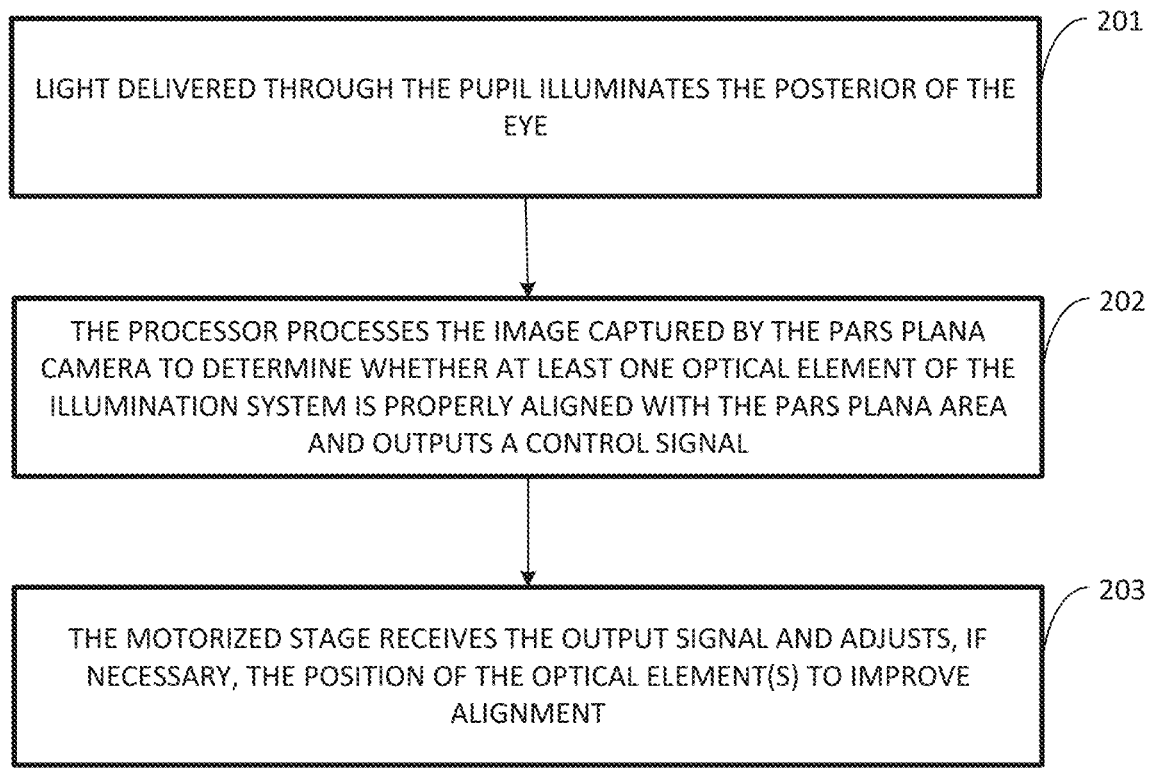
FIG. 11 is flow diagram that represents an example of an algorithm performed by the system shown in FIG. 8.
Figure 12:
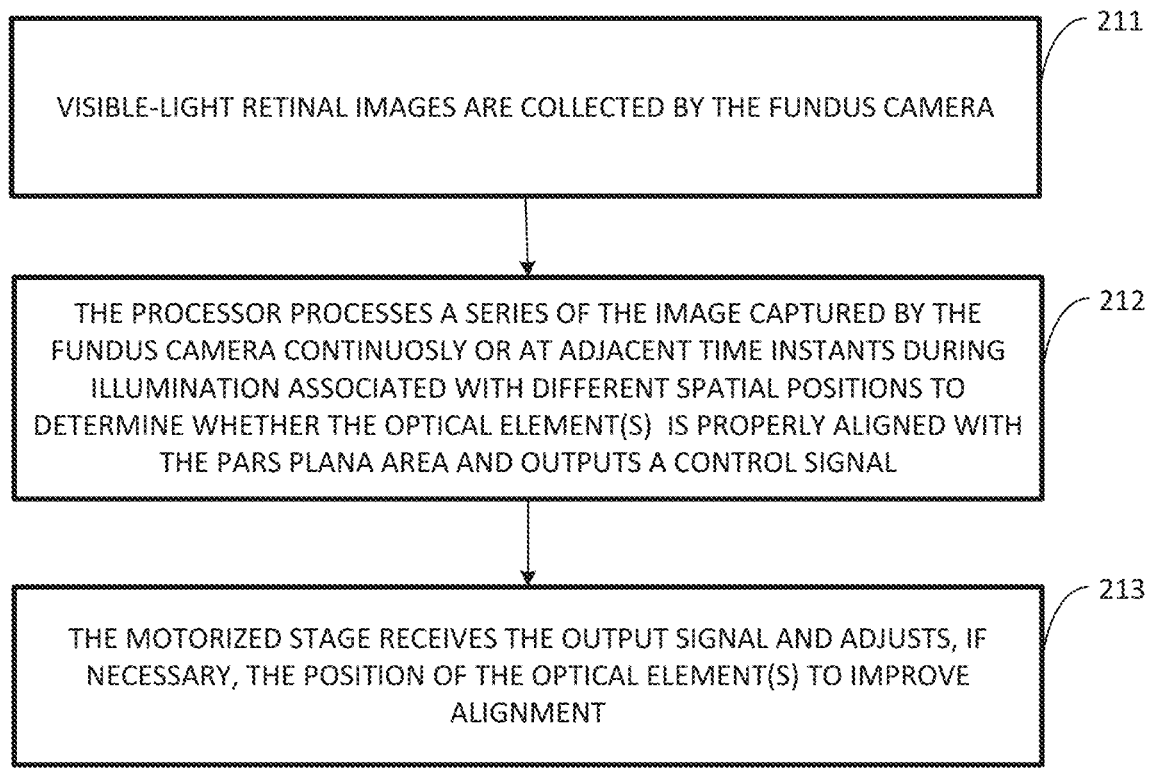
FIG. 12 is flow diagram that represents an example of an algorithm performed by the system shown in FIG. 8.

FIGS. 11 and 12 are flow diagrams that represent these two different algorithms. It should be noted that other algorithms may be used for this purpose, as will be understood by those skilled in the art in view of the description provided herein.

With reference to the flow diagram shown in FIG. 11, light, which is typically NIR light, is delivered through the pupil to illuminate the posterior of the eye, as indicated by block 201. The light scattered from the posterior of the eye, i.e., the retina and choroid, illuminates the sclera. The processor 160 processes the image captured by the optical sensor array of the pars plana camera to determine whether at least one optical element of the illumination system is properly aligned with the pars plana area and outputs a control signal, as indicated by block 202. The motorized stage receives the control signal and adjusts, if necessary, a spatial position of the optical element(s) to improve alignment between the optical element(s) and the pars plana area, as indicated by block 203.

With reference to the flow diagram shown in FIG. 12, the fundus camera 108 collects visible-light retinal images during illumination of the eye with white light, as indicated by block 211. The processor 160 processes a series of the images, either collected continuously or at adjacent instants in time, associated with multiple respective spatial positions of at least one optical element of the optics system of the illumination system to determine which of the spatial positions resulted in proper alignment between the pars plana area and the optical element(s) and outputs a control signal, as indicated by block 212. The motorized stage causes the motorized stage to adjust, if necessary, the position of the optical element(s) to achieve proper alignment, as indicated by block 213.

The algorithms described above are typically implemented in a combination of hardware (e.g., processor 160) and software and/or firmware. The software and/or firmware comprise computer instructions, or code, stored on a non-transitory computer-readable medium (CRM), which is represented by memory 170 shown in FIG. 10. The CRM may be any suitable memory device, including, but not limited to, solid state memory (e.g., random access memory (RAM), read only memory (ROM), erasable programmable read only memory (EPROM), flash memory), magnetic memory devices (e.g., hard drives), optical memory devices (e.g., optical discs) and quantum memory devices.

The foregoing discussion demonstrates that feasibility and practicality of a contact-free, trans-pars-plana illumination for snapshot, widefield fundus photography without the need for pharmacologic pupil dilation. In conventional fundus cameras with trans-scleral illumination, both illumination path and imaging path share the pupil. Typically, the illuminating light is delivered through the periphery of the pupil. In order to minimize the effect of reflections from the cornea and crystalline lens on fundus image, the imaging light is typically collected through the central pupil only. Therefore, the available view of conventional fundus cameras is congenitally limited, and pupil dilation is frequently required for fundus examination of the retinal periphery. Sophisticated system design, with delicate optical devices, were mandatory in those systems to balance the pupil usages for illumination light delivery and imaging light collection, making traditional fundus cameras complex and expensive.

By freeing the entire pupil for collecting imaging light only, the systems described herein dramatically simplify the complexity of the optics system required for widefield fundus photography. Moreover, the trans-pars-planar illumination in accordance with the inventive principles and concepts eliminates all contact parts in previously demonstrated trans-scleral and trans-palpebral illumination for widefield fundus photography. Therefore, the totally contact-free, trans-pars-planar illumination described herein promises next generation low-cost, ultra-widefield, non-mydriatic, snapshot fundus cameras, which will foster clinical deployment of widefield fundus photography to enable better ROP management, early DR detection, and improved accuracy in predicting DR progression and diabetic macular edema (DME) development, etc.

Figure 13:
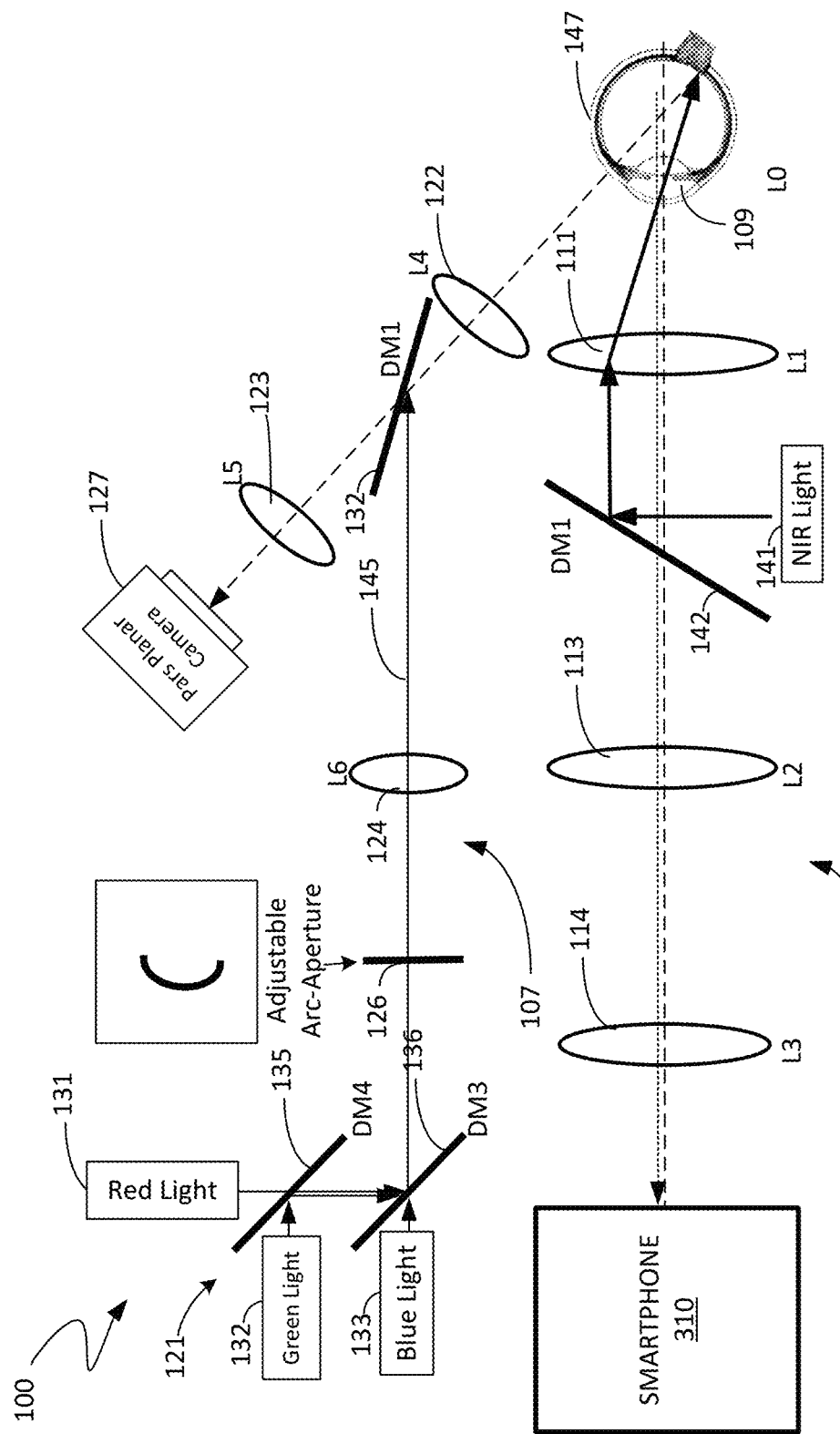
FIG. 13 illustrates a schematic diagram of the non-mydriatic, non-contact u-WF photographic imaging system in accordance with another representative embodiment in which a smartphone is used as the fundus camera.

For example, a smartphone may be used as the fundus camera 8 or 108 of the systems 1 and 100 shown in FIGS. 1 and 8, respectively, to perform widefield, single shot, non-contact, non-mydriatic trans-scleral illumination-based fundus photography. FIG. 13 illustrates a schematic diagram of the non-mydriatic, non-contact u-WF photographic imaging system 300 in accordance with another representative embodiment in which a smartphone 310 is used as the fundus camera. The system 300 is identical to the system 100 shown in FIG. 8 except that the fundus camera 108 shown in FIG. 8 has been replaced in FIG. 13 with the smartphone 310. The smartphone 310 is configured to perform the non-contact, non-mydriatic, single-shot, widefield fundus photography described above with reference to FIGS. 1 and 8. The additional processing of the fundus images described above with reference to FIGS. 4-6 can be performed by a processor of the smartphone 310 or by a processor (e.g., processor 160) to which the smartphone 310 sends the fundus images.

It should be noted that the embodiment of the system 300 shown in FIG. 13 is only one example of the manner in which a smartphone may be used as a fundus camera. Various components could be combined or incorporated into the smartphone 310 or serve as attachments thereto to form a smartphone fundus camera system. Persons of skill in the art will understand, in view of the description provided herein, the manner in which such variations may be made. For example, one or more of the operations described above as being performed by processor 160 and/or various fundus image processing operations such as those described above with reference to FIGS. 4-6 may be performed by a suitably configured processor of the smartphone 310 and/or by a processor of a device (e.g., a personal computer) that is attached to the smartphone 310.

A unique combination of the non-contact, or contact-free, trans-pars-planar illumination, low-cost smartphone technology, quantitative image analysis, and widely available internet technology promises a low-cost, ultra-widefield, non-mydriatic fundus camera to enable affordable telemedicine to reduce health disparities in rural and underserved areas, where both experienced ophthalmologists and expensive devices are limited.

As described above with reference to FIGS. 4-6, there are different color efficiencies for trans-pars-planar illumination. It is known that light attenuation due to absorption and scattering is wavelength dependent. Because the transmission of long wavelength light is much higher than short wavelength light, the LEDs 131-133 shown in FIG. 8 were chosen to have strong short wavelength emission (yellow and green color) and weak long wavelength emission (red color) for trans-pars-planar illumination. However, the fundus images were still red predominated. It is well established that details of retinal vasculatures are mainly reflected in short wavelength images. In order to produce retinal blood vessel enhanced images, the above discussion demonstrates the feasibility of digitally normalizing intensity values of individual color channels. However, the effective dynamic ranges of red, green, and blue channels can be different for trans-pars-planar illumination with a single light source. For example, when the red channel is close to saturation level (i.e. 255 for an 8-bit camera), the green channel may only have a light level of ~60. In other words, the effective dynamic range of the green channel is only ~¼ provided by the camera sensor.

By comprising the light source 121 of separate red, green and blue LEDs 131-133, respectively, individual R/G/B power controls can be used to compensate for color difference of light efficiency of ocular tissues, and thus to maximize useful dynamic range of the digital camera. For example, the processor 160 can be configured to perform an algorithm that causes the power delivered to the LEDs 131-133 to be adjusted, as needed, to control the relative percentages of red, green and blue light that are combined to form the illumination light.

Through experimentation, it was determined that prolonged exposure time can blur fundus images due to involuntary eye movements. The inventors performed testing with flash light sources to pursue improved quality of fundus images and determined that increased light power can be used to control exposure time to millisecond level to minimize the effect of eye movements on fundus image. In other words, the fundus camera can be configured to reduce exposure time to avoid blur, given the power of the illumination light that is being directed onto the pars plana is sufficiently high.

It should be noted that the illustrative embodiments have been described with reference to a few embodiments for the purpose of demonstrating the principles and concepts of the invention. Persons of skill in the art will understand how the principles and concepts of the invention can be applied to other embodiments not explicitly described herein. For example, while particular system arrangements are described herein and shown in the figures, a variety of other system configurations may be used. As will be understood by those skilled in the art in view of the description provided herein, many modifications may be made to the embodiments described herein while still achieving the goals of the invention, and all such modifications are within the scope of the invention.

What is claimed is:

1. A non-mydriatic, non-contact ultra-widefield fundus (u-WF) photographic imaging system for imaging an eye, the system comprising:
   an illumination system comprising:
      at least a first light source, the first light source generating light of at least a first wavelength range;
      a first optics system, the first optics system being configured to convert the light into a first light beam having a first predetermined shape and size, the first optics system including at least a first optical element that is spaced a predetermined distance away from an eyeball to avoid physical contact with the eyeball and with an eyelid of the eye, the first optical element being configured to couple the first light beam onto a pars plana area of an eyeball, wherein the first optics system includes at least an aperture element having an annular-arc shape to cause the first predetermined shape of the first light beam to substantially match a shape of the pars plana area of the eyeball, wherein the aperture element is configured to be positioned between the first optical element and the pars plana area of the eyeball;
   at least a second light source of a second optics system, the second light source generating light of at least a second wavelength range during an alignment process of the first optics system between the pars plana area and the first optical element of the first optics system;
   at least a second optical element of the second optics system arranged with respect to the second light source to couple at least a portion of the light of the second wavelength range through a pupil of the eye to illuminate a posterior region of the eyeball during the alignment process of the first optics system, wherein at least a portion of the light of the second wavelength range that illuminates the posterior region is scattered from the posterior region onto a sclera of the eyeball; and
   a second optical sensor array positioned to receive at least a portion of the light scattered onto the sclera and configured to produce a second image from the portion of the scattered light received thereby, the second image containing information relating to the alignment between the pars plana area and the first optical element of the first optics system; and
   at least a processor configured to process the second image to determine whether the first optical element is properly aligned with the pars plana area and to output a first control signal; and
   at least a first motorized stage mechanically coupled to the first optical element, the first motorized stage receiving the first control signal and adjusting a spatial position of the first optical element to improve alignment between the first optical element and the pars plana area.

2. The non-mydriatic, non-contact u-WF photographic imaging system of claim 1, wherein the second light source is a near-infrared (NIR) light source and the second wavelength range is an NIR wavelength range.

3. The non-mydriatic, non-contact u-WF photographic imaging system of claim 2, wherein the first light source generates white light and the first wavelength range includes wavelengths in a visible spectrum.

4. The non-mydriatic, non-contact u-WF photographic imaging system of claim 3, wherein the first light source comprises a red light source that generates red light, a green light source that generates green light and a blue light source that generates blue light, the first optics system combining the red light, the green light and the blue light to produce the white light.

5. The non-mydriatic, non-contact u-WF photographic imaging system of claim 4, further comprising:
   an imaging system comprising:
      a second optics system, the second optics system being configured to receive light at the first wavelength range passing out of a pupil of the eyeball over an ultra-wide field of view (FOV) and to direct at least a portion of the received light in a first direction; and
      a first camera, the first camera having a first optical sensor array, at least a portion of the light at the first wavelength range directed in the first direction being incident on the first optical sensor array, the first optical sensor array being configured to produce a first fundus photographic image from the incident light, wherein said at least a processor is configured to process the first fundus photographic image and, if necessary, to make an adjustment to an amount of electrical power delivered to at least one of the red, green and blue light sources in order to control relative percentages of red, green and blue light that are combined by the first optics system to produce the white light.

6. The non-mydriatic, non-contact u-WF photographic imaging system of claim 5, wherein the first camera is a camera of a smartphone.

7. The non-mydriatic, non-contact u-WF photographic imaging system of claim 5, wherein the first camera reduces exposure time to avoid blur.

8. The non-mydriatic, non-contact u-WF photographic imaging system of claim 1, wherein the second light source is a near-infrared (NIR) light source and the second wavelength range is an NIR wavelength range.

9. The non-mydriatic, non-contact u-WF photographic imaging system of claim 8, wherein the first light source generates white light and the first wavelength range includes wavelengths in a visible spectrum.

10. The non-mydriatic, non-contact u-WF photographic imaging system of claim 9, wherein the first light source comprises a red light source that generates red light, a green light source that generates green light and a blue light source that generates blue light, the first optics system combining the red light, the green light and the blue light to produce the white light.

11. The non-mydriatic, non-contact u-WF photographic imaging system of claim 10, further comprising:
an imaging system comprising:
a second optics system, the second optics system being configured to receive light at the first wavelength range passing out of a pupil of the eyeball over an ultra-wide field of view (FOV) and to direct at least a portion of the received light in a first direction; and
a first camera, the first camera having a first optical sensor array, at least a portion of the light at the first wavelength range directed in the first direction being incident on the first optical sensor array, the first optical sensor array being configured to produce a first fundus photographic image from the incident light,
wherein said at least a processor is configured to process the first fundus photographic image and, if necessary, to make an adjustment to an amount of electrical power delivered to at least one of the red, green and blue light sources in order to control relative percentages of red, green and blue light that are combined by the first optics system to produce the white light.

12. The non-mydriatic, non-contact u-WF photographic imaging system of claim 1, wherein the first optical element is a lens.

13. A non-mydriatic, non-contact u-WF photographic imaging system, comprising:
an illumination system comprising:
at least a first light source, the first light source generating light of at least a first wavelength range;
a first optics system, the first optics system being configured to convert the light into a first light beam having a first predetermined shape and size, the first optics system including at least a first optical element that is spaced a predetermined distance away from an eyeball to avoid physical contact with the eyeball and with an eyelid of the eye, the first optical element being configured to couple the first light beam onto a pars plana area of an eyeball, wherein the first optics system includes at least an aperture element having an annular-arc shape to cause the first predetermined shape of the first light beam to substantially match a shape of the pars plana area of the eyeball, wherein the aperture element is configured to be positioned between the first optical element and the pars plana area of the eyeball;
an imaging system comprising:
a second optics system, the second optics system being configured to receive light at the first wavelength range passing out of a pupil of the eyeball over an ultra-wide field of view (FOV) and to direct at least a portion of the received light in a first direction; and
a first camera, the first camera having a first optical sensor array, at least a portion of the light at the first wavelength range directed in the first direction being incident on the first optical sensor array, the first optical sensor array being configured to produce a first fundus photographic image from the incident light; and
at least a processor configured to process a series of the first fundus photographic images produced by the first optical sensor array at multiple instants in time associated with multiple respective spatial positions of the first optical element of the first optics system to determine which of the spatial positions resulted in proper alignment between the pars plana area and the first optical element and to output a first control signal; and
at least a first motorized stage mechanically coupled to the first optical element, the first motorized stage receiving the first control signal and, if the first control signal indicates that the first optical element is not properly aligned with the pars plana area, moving the first optical element to the spatial position that resulted in proper alignment between the first optical element and the pars plana area.

14. A method for performing non-mydriatic, non-contact ultra-widefield fundus (u-WF) photographic imaging of an eye, the method comprising:
with at least a first light source, generating light of at least a first wavelength range;
with a first optics system, converting the light into a first light beam having a first predetermined shape and size, the first optics system including at least a first optical element that is spaced a predetermined distance away from an eyeball to avoid physical contact with the eyeball and with an eyelid of the eye, wherein the first optics system further includes an aperture element having an annular-arc shape to cause the first predetermined shape of the first light beam to substantially match a shape of a pars plana area of the eyeball, wherein the aperture element is positioned between the first optical element and the pars plana area of the eyeball;
with the first optical element, coupling the first light beam onto the pars plana area of an eyeball;
with a second optics system, receiving light at the first wavelength range passing out of a pupil of the eyeball over an ultra-wide field of view (FOV) and directing at least a portion of the received light in a first direction;
with a first optical sensor array of a first camera, receiving at least a portion of the light at the first wavelength range directed in the first direction and producing a first fundus photographic image from the light received by the first optical sensor array;

with at least a second light source, generating light of at least a second wavelength range during an alignment process of the first optics system between the pars plana area and the first optical element of the first optics system; and with at least a second optical element of a second optics system, coupling at least a portion of the light of the second wavelength range through the pupil to illuminate a posterior region of the eyeball, wherein at least a portion of the light of the second wavelength range that illuminates the posterior region is scattered from the posterior region onto a sclera of the eyeball;

with a second optical sensor array, receiving at least a portion of the light scattered onto the sclera and producing a second image from the portion of the scattered light received thereby, the second image containing information relating to the alignment between the pars plana area and the first optical element of the first optics system;

with a processor, processing the second image to determine whether the first optical element is properly aligned with the pars plana area and to output a first control signal; and with the at least a motorized stage mechanically coupled to the first optical element, receiving the first control signal and adjusting a spatial position of the first optical element to improve alignment between the first optical element and the pars plana area.

15. The method of claim 14, wherein the first optical element is a lens.

16. A non-mydriatic, non-contact u-WF photographic imaging system comprising:
an illumination system comprising:
at least a first light source, the first light source generating light of at least a first wavelength range;
a first optics system, the first optics system being configured to convert the light into a first light beam having a first predetermined shape and size, the first optics system including at least a first optical element that is spaced a predetermined distance away from an eyeball to avoid physical contact with the eyeball and with an eyelid of the eye, the first optical element being configured to couple the first light beam onto a pars plana area of an eyeball, wherein the first optics system includes at least an aperture element having an annular-arc shape to cause the first predetermined shape of the first light beam to substantially match a shape of the pars plana area of the eyeball, wherein the aperture element is configured to be positioned between the first optical element and the pars plana area of the eyeball;
at least a second light source of a second optics system, the second light source generating light of at least a second wavelength range during an alignment process of the first optics system between the pars plana area and the first optical element of the first optics system;
at least a second optical element of the second optics system arranged with respect to the second light source to couple at least a portion of the light of the second wavelength range through a pupil of the eye to illuminate a posterior region of the eyeball during the alignment process of the first optics system, wherein at least a portion of the light of the second wavelength range that illuminates the posterior region is scattered from the posterior region onto a sclera of the eyeball;
a second optical sensor array positioned to receive at least a portion of the light scattered onto the sclera and configured to produce a second image from the portion of the scattered light received thereby, the second image containing information relating to the alignment between the pars plana area and the first optical element of the first optics system; and
at least a processor configured to process the second image to determine whether the first optical element is properly aligned with the pars plana area and to output a first control signal; and adjust the arc-shaped aperture element to allow a width of an arc-shaped pattern formed by the arc-shaped aperture element to be adjusted to match the size of the pars plana area.

17. A method for performing non-mydriatic, non-contact ultra-widefield fundus (u-WF) photographic imaging of an eye, of comprising:
with at least a first light source, generating light of at least a first wavelength range;
with a first optics system, converting the light into a first light beam having a first predetermined shape and size, the first optics system including at least a first optical element that is spaced a predetermined distance away from an eyeball to avoid physical contact with the eyeball and with an eyelid of the eye, wherein the first optics system further includes an aperture element having an annular-arc shape to cause the first predetermined shape of the first light beam to substantially match a shape of a pars plana area of the eyeball, wherein the aperture element is positioned between the first optical element and the pars plana area of the eyeball;
with the first optical element, coupling the first light beam onto the pars plana area of an eyeball;
with at least a second light source, generating light of at least a second wavelength range during an alignment process of the first optics system between the pars plana area and the first optical element of the first optics system; and
with at least a second optical element of a second optics system, coupling at least a portion of the light of the second wavelength range through a pupil of the eye to illuminate a posterior region of the eyeball, wherein at least a portion of the light of the second wavelength range that illuminates the posterior region is scattered from the posterior region onto a sclera of the eyeball;
with a second optical sensor array, receiving at least a portion of the light scattered onto the sclera and producing a second image from the portion of the scattered light received thereby, the second image containing information relating to the alignment between the pars plana area and the first optical element of the first optics system;
with a processor, processing the second image to determine whether the first optical element is properly aligned with the pars plana area and to output a first control signal; and
with the processor, adjusting the arc-shaped aperture element to allow a width of an arc-shaped pattern formed by the arc-shaped aperture element to be adjusted to match the size of the pars plana area.

* * * * *